(12) United States Patent
Aouad

(10) Patent No.: US 12,319,898 B2
(45) Date of Patent: *Jun. 3, 2025

(54) LAUNDRY SCENT ADDITIVE

(71) Applicant: The Procter & Gamble Company, Cincinnati, OH (US)

(72) Inventor: Yousef Georges Aouad, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/911,576

(22) Filed: Oct. 10, 2024

(65) Prior Publication Data

US 2025/0101345 A1 Mar. 27, 2025

Related U.S. Application Data

(63) Continuation of application No. 18/488,460, filed on Oct. 17, 2023, now Pat. No. 12,139,692, which is a continuation of application No. 18/378,833, filed on Oct. 11, 2023, now Pat. No. 12,006,492, which is a continuation of application No. 18/484,094, filed on Oct. 10, 2023, now abandoned, which is a continuation of application No. 18/143,330, filed on May 4, 2023, now Pat. No. 11,834,637, which is a continuation of application No. 18/127,878, filed on Mar. 29, 2023, which is a continuation of application No. 18/122,851, filed on Mar. 17, 2023, now Pat. No. 12,104,146, which is a continuation of application No. 18/122,797, filed on Mar. 17, 2023, now Pat. No. 12,104,145, which is a continuation of application No. 18/122,378, filed on Mar. 16, 2023, now abandoned, which is a continuation of application No. 18/110,123, filed on Feb. 15, 2023, now Pat. No. 11,753,606, which is a continuation of application No. 18/109,621, filed on Feb. 14, 2023, now Pat. No. 11,859,159, which is a continuation of application No. 17/471,590, filed on Sep. 10, 2021, now Pat. No. 11,608,481, which is a continuation of application No. 16/201,596, filed on Nov. 27, 2018, now Pat. No. 11,142,728, which is a continuation of application No. 15/626,482, filed on Jun. 19, 2017, now Pat. No. 10,167,441, which is a continuation of application No. 13/908,514, filed on Jun. 3, 2013, now Pat. No. 9,708,574, which is a continuation of application No. 13/462,157, filed on May 2, 2012, now Pat. No. 8,476,219, which is a continuation of application No. PCT/US2010/055398, filed on Nov. 4, 2010.

(30) Foreign Application Priority Data

Nov. 5, 2009 (CA) .................... CA 2682636

(51) Int. Cl.
| | | |
|---|---|---|
| C11D 3/50 | (2006.01) | |
| B29C 41/02 | (2006.01) | |
| B65D 83/06 | (2006.01) | |
| C11D 3/12 | (2006.01) | |
| C11D 3/20 | (2006.01) | |
| C11D 3/37 | (2006.01) | |
| C11D 3/40 | (2006.01) | |
| C11D 17/04 | (2006.01) | |
| D06M 13/00 | (2006.01) | |
| D06M 15/53 | (2006.01) | |
| D06M 23/12 | (2006.01) | |

(52) U.S. Cl.
CPC .............. *C11D 3/505* (2013.01); *B29C 41/02* (2013.01); *B65D 83/06* (2013.01); *C11D 3/128* (2013.01); *C11D 3/2068* (2013.01); *C11D 3/2072* (2013.01); *C11D 3/2093* (2013.01); *C11D 3/3707* (2013.01); *C11D 3/40* (2013.01); *C11D 17/046* (2013.01); *D06M 13/005* (2013.01); *D06M 15/53* (2013.01); *D06M 23/12* (2013.01); *C11D 2111/12* (2024.01)

(58) Field of Classification Search
CPC .... C11D 3/50; C11D 3/12; C11D 3/20; C11D 3/37; C11D 3/40; B29C 41/02
USPC ........................................ 512/4, 1
See application file for complete search history.

(56) References Cited

U.S. PATENT DOCUMENTS

| | | |
|---|---|---|
| 3,664,963 A | 5/1972 | Pasin |
| 4,026,131 A | 5/1977 | Dugger et al. |
| 4,176,079 A | 11/1979 | Guerry et al. |
| 4,209,417 A | 6/1980 | Whyte |
| 4,234,627 A | 11/1980 | Schilling |
| 4,236,882 A | 12/1980 | Weinhold |
| 4,253,842 A | 3/1981 | Ehrlich |

(Continued)

FOREIGN PATENT DOCUMENTS

| | | |
|---|---|---|
| DE | 2263940 A1 | 7/1974 |
| EP | 0391087 A1 | 10/1990 |

(Continued)

OTHER PUBLICATIONS

U.S. Appl. No. 18/143,330-B2, filed Nov. 15, 2023, Aouad; Yousef Georges.*

(Continued)

*Primary Examiner* — Jessica Whiteley

(74) *Attorney, Agent, or Firm* — Carolyn S. Powell; George H. Leal

(57) ABSTRACT

A laundry scent additive having polyethylene glycol repeat units and perfume. The laundry scent additive enables consumers to control the amount of scent imparted to their laundry.

30 Claims, 1 Drawing Sheet

(56) References Cited

U.S. PATENT DOCUMENTS

| | | |
|---|---|---|
| 4,264,466 A | 4/1981 | Carleton et al. |
| 4,279,579 A | 7/1981 | Froeschke |
| 4,365,853 A | 12/1982 | Ehrlich |
| 4,416,791 A | 11/1983 | Haq |
| 4,514,461 A | 4/1985 | Woo |
| 4,557,852 A | 12/1985 | Schulz et al. |
| 4,597,959 A | 7/1986 | Barr |
| 4,765,916 A | 8/1988 | Ogar, Jr. et al. |
| 4,882,220 A | 11/1989 | Ono et al. |
| 4,898,781 A | 2/1990 | Onouchi et al. |
| 5,004,556 A | 4/1991 | Julemont et al. |
| 5,013,498 A | 5/1991 | Froeschke |
| 5,160,654 A | 11/1992 | Falou et al. |
| 5,185,155 A | 2/1993 | Behan et al. |
| 5,328,684 A | 7/1994 | Morgan et al. |
| 5,384,186 A | 1/1995 | Trinh |
| 5,407,594 A | 4/1995 | Fry et al. |
| 5,614,179 A | 3/1997 | Murphy et al. |
| 5,733,272 A | 3/1998 | Brunner et al. |
| 5,770,235 A | 6/1998 | Baumann et al. |
| 5,817,614 A | 10/1998 | Miracle et al. |
| 5,858,957 A * | 1/1999 | Donoghue .............. C11D 17/06 510/351 |
| 5,955,057 A | 9/1999 | Maunder et al. |
| 6,022,845 A | 2/2000 | Avila-garcia |
| 6,025,319 A | 2/2000 | Surutzidis et al. |
| 6,037,319 A | 3/2000 | Dickler |
| 6,048,830 A | 4/2000 | Gallon et al. |
| 6,121,215 A | 9/2000 | Rau |
| 6,183,661 B1 | 2/2001 | Makin et al. |
| 6,200,949 B1 | 3/2001 | Reijmer et al. |
| 6,287,550 B1 | 9/2001 | Trinh |
| 6,410,051 B1 | 6/2002 | Georg et al. |
| 6,410,500 B1 | 6/2002 | Haerer et al. |
| 6,468,950 B1 | 10/2002 | Kawasaki et al. |
| 6,514,429 B1 | 2/2003 | Waschenbach et al. |
| 6,551,983 B1 | 4/2003 | Welch |
| 6,645,479 B1 | 11/2003 | Shefer et al. |
| 6,730,646 B1 | 5/2004 | Waschenbach et al. |
| 6,825,161 B2 | 11/2004 | Shefer et al. |
| 7,056,877 B2 | 6/2006 | Caswell et al. |
| 7,091,171 B2 | 8/2006 | Caswell et al. |
| 7,119,057 B2 | 10/2006 | Popplewell |
| 7,125,835 B2 | 10/2006 | Bennett |
| 7,166,565 B2 | 1/2007 | Caswell et al. |
| 7,186,680 B2 | 3/2007 | Caswell |
| 7,196,049 B2 | 3/2007 | Brain |
| 7,867,968 B1 | 1/2011 | Aouad |
| 7,871,976 B1 | 1/2011 | Aouad |
| 8,476,219 B2 | 7/2013 | Aouad |
| 9,108,574 B1 | 8/2015 | Shen |
| 9,453,189 B2 | 9/2016 | Aouad |
| 9,708,574 B2 * | 7/2017 | Aouad ................. C11D 3/2068 |
| 10,167,441 B2 * | 1/2019 | Aouad ................... B65D 83/06 |
| 11,142,728 B2 | 10/2021 | Aouad |
| 11,608,481 B2 | 3/2023 | Aouad |
| 11,753,606 B2 * | 9/2023 | Aouad ................... C11D 3/128 264/297.1 |
| 11,834,637 B2 | 12/2023 | Aouad |
| 11,859,159 B2 | 1/2024 | Aouad |
| 12,006,492 B2 | 6/2024 | Aouad |
| 12,091,644 B2 | 9/2024 | Aouad |
| 12,104,145 B2 | 10/2024 | Aouad |
| 12,104,146 B2 * | 10/2024 | Aouad ................. C11D 3/2093 |
| 12,139,692 B2 | 11/2024 | Aouad |
| 2001/0023017 A1 | 9/2001 | Tararuj et al. |
| 2002/0137657 A1 | 9/2002 | Lant |
| 2003/0096730 A1 | 5/2003 | Perring et al. |
| 2003/0099733 A1 | 5/2003 | Lumley |
| 2003/0104969 A1 | 6/2003 | Caswell et al. |
| 2003/0158344 A1 | 8/2003 | Rodrigues et al. |
| 2003/0165692 A1 | 9/2003 | Koch et al. |
| 2003/0195133 A1 | 10/2003 | Shefer et al. |
| 2003/0203829 A1 | 10/2003 | Shefer et al. |
| 2003/0215417 A1 | 11/2003 | Uchiyama |
| 2003/0216488 A1 | 11/2003 | Uchiyama |
| 2004/0029765 A1 | 2/2004 | Weber |
| 2004/0071746 A1 | 4/2004 | Popplewell et al. |
| 2004/0072720 A1 | 4/2004 | Brain et al. |
| 2004/0087477 A1 | 5/2004 | Ness |
| 2004/0106536 A1 | 6/2004 | Mane et al. |
| 2004/0241195 A1 | 12/2004 | Tollens |
| 2005/0026793 A1 | 2/2005 | Caswell et al. |
| 2005/0227905 A1 | 10/2005 | Heinz et al. |
| 2006/0039934 A1 | 2/2006 | Ness et al. |
| 2006/0076370 A1 | 4/2006 | Etesse |
| 2007/0269651 A1 | 11/2007 | Denome et al. |
| 2008/0014393 A1 | 1/2008 | Denome et al. |
| 2008/0032909 A1 | 2/2008 | De Buzzaccarini et al. |
| 2008/0131695 A1 | 6/2008 | Aouad et al. |
| 2008/0136055 A1 | 6/2008 | Cook et al. |
| 2008/0200363 A1 | 8/2008 | Smets |
| 2009/0042766 A1 | 2/2009 | Mayer et al. |
| 2009/0215664 A1 | 8/2009 | Raehse |
| 2009/0305936 A1 | 12/2009 | Busch et al. |
| 2010/0022437 A1 | 1/2010 | Artiga-gonzalez |
| 2010/0115708 A1 | 5/2010 | Caswell et al. |
| 2014/0057825 A1 | 2/2014 | Denome et al. |
| 2019/0144797 A1 | 5/2019 | Aouad |
| 2021/0403835 A1 | 12/2021 | Aouad |
| 2023/0193166 A1 | 6/2023 | Aouad |
| 2023/0287309 A1 | 9/2023 | Aouad |
| 2023/0287310 A1 | 9/2023 | Aouad |
| 2023/0295535 A1 | 9/2023 | Aouad |
| 2024/0034964 A1 | 2/2024 | Aouad |
| 2024/0043776 A1 | 2/2024 | Aouad |
| 2024/0110133 A1 | 4/2024 | Aouad |

FOREIGN PATENT DOCUMENTS

| | | |
|---|---|---|
| EP | 0628627 A1 | 12/1994 |
| EP | 0812808 A1 | 12/1997 |
| EP | 0938923 A1 | 9/1999 |
| GB | 1487746 A | 10/1977 |
| GB | 2204825 A | 11/1988 |
| GB | 2235206 A | 2/1991 |
| JP | 05168686 | 7/1993 |
| WO | 9308255 A1 | 4/1993 |
| WO | 9404656 A2 | 3/1994 |
| WO | 9909136 A1 | 2/1999 |
| WO | 0185888 A2 | 11/2001 |
| WO | 0226928 A1 | 4/2002 |
| WO | 2004020566 A1 | 3/2004 |
| WO | 2004105811 A1 | 12/2004 |
| WO | 2005097962 A1 | 10/2005 |
| WO | 2008009521 A1 | 1/2008 |
| WO | 2009071373 A1 | 6/2009 |

OTHER PUBLICATIONS

All Office Actions: U.S. Appl. No. 18/122,378, filed Mar. 16, 2023.
All Office Actions: U.S. Appl. No. 18/122,797, filed Mar. 17, 2023.
All Office Actions: U.S. Appl. No. 18/122,851, filed Mar. 17, 2023.
All Office Actions; U.S. Appl. No. 18/538,837, filed Dec. 13, 2023.
All Office Actions; U.S. Appl. No. 12/732,576, filed Mar. 26, 2010.
All Office Actions; U.S. Appl. No. 12/749,747, filed Mar. 30, 2010.
All Office Actions; U.S. Appl. No. 13/462,157, filed May 2, 2012.
All Office Actions; U.S. Appl. No. 15/626,482, filed Jun. 19, 2017.
All Office Actions; U.S. Appl. No. 17/471,590, filed Sep. 10, 2021.
All Office Actions; U.S. Appl. No. 18/109,621, filed Feb. 14, 2023.
All Office Actions; U.S. Appl. No. 18/110,123, filed Feb. 15, 2023.
All Office Actions; U.S. Appl. No. 18/127,878, filed Mar. 29, 2023.
All Office Actions; U.S. Appl. No. 18/378,833, filed Oct. 11, 2023.
All Office Actions; U.S. Appl. No. 18/484,094, filed Oct. 10, 2023.
All Office Actions; U.S. Appl. No. 18/488,460, filed Oct. 17, 2023.
All Office Actions; U.S. Appl. No. 16/201,596, filed Nov. 27, 2018.
All Office Actions; U.S. Appl. No. 18/143,330, filed May 4, 2023.
Grounds for Appeal, Opposition of EP2496679B1 dated Feb. 12, 2018.
Letter in Reply to Grounds of Appeal and Auxiliary Requests 1-4 filed by Henkel AG & Co. KGaA for EP Patent Application No. 10779153.5, dated Jun. 22, 2018.

(56) References Cited

OTHER PUBLICATIONS

Opposition of EP2496679B1 Letter by Proprietor P&G in Reply to Communication of the Board of Appeal, dated Dec. 3, 2020, 11 Pages.
Opposition of EP2496679B1, Decision Patent Maintained as Granted, dated Sep. 25, 2017.
Opposition of EP2496679B1, EPO Board of Appeal Provisional Opinion dated Aug. 4, 2020.
Opposition of EP2496679B1, EPO Board of Appeal Provisional Opinion dated Dec. 3, 2020.
Opposition of EP2496679B1, Letter by Opponent Henkel dated Jan. 29, 2018.
Opposition of EP2496679B1, Minutes, Opening of Oral Proceedings, dated Oct. 31, 2017.
Opposition of EP249679B1 Decision of Technical Board of Appeal dated Sep. 14, 2021, 28 pages.
Opposition of EP249679B1 Letter by Opponent Henkel, dated Aug. 11, 2021, 16 Pages.
Opposition of EP249679B1 Minutes of the Oral Proceedings, dated Sep. 14, 2021, 3 Pages.
R.G. Berger, Springer. "Flavours and Fragrances", Year 2007, 5 Pages.
Reply from Opposition Division including a redressed complete version of the oral proceedings minutes for Application/Patent No. 10779153.5-1375 / 2496679, dated Oct. 31, 2017.
Reza Arshady et al."Microcapsule Patents and Products", Citrus books, Year 2003, 7 Pages.
URL link; https://www.alfa.com/de/catalog/A16151.

\* cited by examiner

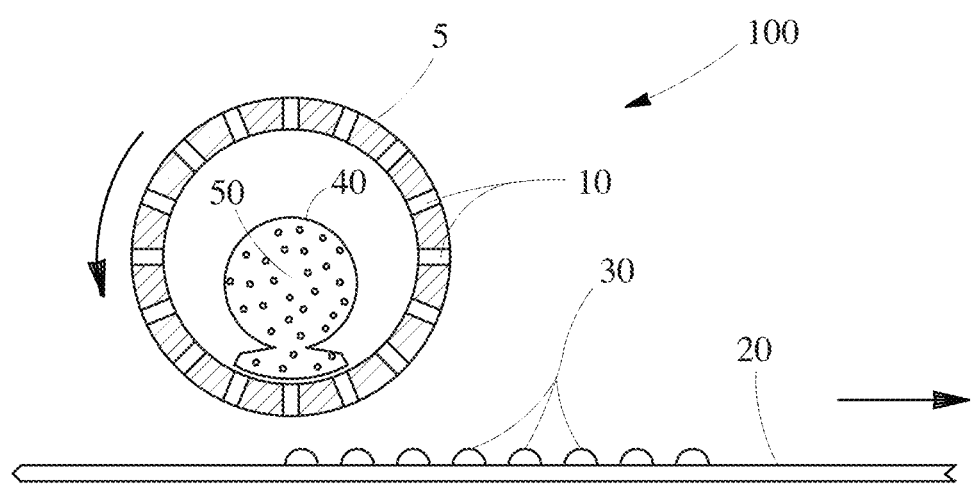

LAUNDRY SCENT ADDITIVE

FIELD OF THE INVENTION

The present invention relates to products to freshen laundry.

BACKGROUND OF THE INVENTION

There is a segment of consumers that prefer a strong perfume scent to their laundry. These so called "scent seekers" will often over dose laundry products such as laundry detergent and fabric softener to provide the desired freshness to their laundry. There is a need to provide a perfume scent additive product to consumer that will provide freshness to laundry. Such scent additive needs to be able to be applied by the consumer, independent of other laundry products, to achieve the desired scent level in a cost effective manner.

SUMMARY OF THE INVENTION

An embodiment of the invention can be a composition consisting essentially of: (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of friable perfume microcapsule, wherein the perfume microcapsule comprises encapsulated perfume; wherein the composition is shaped in a pastille having a mass from about 0.95 mg to about 2 g.

An additional embodiment of the invention can be a unit dose of a fabric treatment composition comprising a plurality of pastilles, wherein each pastille comprises: (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of friable perfume microcapsule, wherein the perfume microcapsule comprises encapsulated perfume; wherein each pastille has a mass from about 0.95 mg to about 2 g; and wherein the plurality of pastilles has a mass from about 13 g to about 27 g to comprise the unit dose.

An additional embodiment of the invention can be a composition consisting essentially of: (a) from about 80% to about 91% by weight of the composition of polyethylene glycol, wherein the polyethylene glycol has a molecular weight from about 5,000 to about 11,000; and (b) from about 9% to about 20 wt % of friable perfume microcapsule, wherein the perfume microcapsule comprises encapsulated perfume; wherein the composition is essentially free of free perfume; and wherein the composition is shaped in a pastille having a mass from about 0.95 mg to about 2 g.

An additional embodiment of the invention can be a composition consisting essentially of: (a) from about 80% to about 91% by weight of the composition of polyethylene glycol, wherein the polyethylene glycol has a molecular weight from about 5,000 to about 11,000; and (b) from about 9% to about 20% by weight of the composition free perfume; wherein the composition is essentially free of a perfume carrier; and wherein the composition is shaped in a pastille having a mass from about 0.95 mg to about 2 g.

An additional embodiment of the invention can be a method of making a composition comprising the steps of: providing a viscous material having a glass transition temperature, the viscous material comprising: (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of perfume microcapsule, wherein the perfume microcapsule comprises encapsulated perfume; providing the viscous material at a processing temperature less than about 20 degrees Celsius higher than the glass transition temperature; and passing the viscous material through small openings and onto a moving conveyor surface upon which the viscous material is cooled below the glass transition temperature to form a plurality of pastilles.

BRIEF DESCRIPTION OF THE DRAWING

FIG. 1 is a schematic of a pastillation apparatus.

DETAILED DESCRIPTION OF THE INVENTION

The compositions of the present invention may comprise: polyethylene glycol; free perfume and/or perfume microcapsules; and optionally a dye. In one embodiment, the composition is essentially free of detergent surfactants and/or fabric softening actives.

Polyethylene Glycol (PEG)

Polyethylene glycol (PEG) has a relatively low cost, may be formed into many different shapes and sizes, minimizes free perfume diffusion, and dissolves well in water. PEG comes in various molecular weights. A suitable molecular weight range of PEG for the purposes of freshening laundry includes from about 3,000 to about 13,000, from about 4,000 to about 12,000, alternatively from about 5,000 to about 11,000, alternatively from about 6,000 to about 10,000, alternatively from about 6,000 to about 10,000, alternatively from about 7,000 to about 9,000, alternatively combinations thereof. PEG is available from BASF, for example PLURIOL E 8000.

The compositions of the present invention may comprise from about 65% to about 99% by weight of the composition of PEG. Alternatively, the composition can comprise from about 80% to about 91%, alternatively from about 85% to about 91%, more than about 75%, alternatively from about 70% to about 98%, alternatively from about 80% to about 95%, alternatively combinations thereof, of PEG by weight of the composition.

Free Perfume

The compositions of the present invention may comprise a free perfume and/or a perfume microcapsule. Perfumes are generally described in U.S. Pat. No. 7,186,680 at column 10, line 56, to column 25, line 22. In one embodiment, the composition comprises free perfume and is essentially free of perfume carriers, such as a perfume microcapsule. In yet another embodiment, the composition comprises perfume carrier materials (and perfume contained therein). Examples of perfume carrier materials are described in U.S. Pat. No. 7,186,680, column 25, line 23, to column 31, line 7. Specific examples of perfume carrier materials may include cyclodextrin and zeolites.

In one embodiment, the composition comprises free (neat) perfume but is free or essentially free of a perfume carrier. In such an embodiment, the composition may comprise less than about 20%, alternatively less than about 25%, alternatively from about 9% to about 20%, alternatively from about 10% to about 18%, alternatively from about 11% to about 13%, alternatively combinations thereof, of free perfume by weight of the composition.

In one embodiment, the composition consists essentially of: (a) from about 80% to about 91% by weight of the composition of polyethylene glycol, wherein the polyethylene glycol has a molecular weight from about 5,000 to about 11,000; and (b) from about 9% to about 20% by weight of the composition free perfume; wherein the composition is essentially free of a perfume carrier; and wherein the composition is shaped in a pastille having a mass from about 0.95 mg to about 2 g. In an alternative embodiment, the composition consists essentially of: (a) more than about 75% by weight of the composition of polyethylene glycol, wherein the polyethylene glycol has a molecular weight from about 5,000 to about 11,000; and (b) less than about 25% by weight of the composition free perfume; wherein the composition is essentially free of a perfume carrier; and wherein the composition is shaped in a pastille having a mass from about 0.95 mg to about 2 g.

In another embodiment, the composition comprises free perfume and perfume microcapsules. In this embodiment, the composition may comprise from about 2% to about 12%, alternatively from about 1% to about 10%, alternatively from about 3% to about 8%, alternatively from about 4% to about 7%, alternatively from about 5% to about 7%, alternatively combinations thereof, of the free perfume by weight of the composition.

In yet another embodiment, the composition comprises free (neat) perfume and a perfume microcapsule but is free or essentially free of other perfume carriers.

Perfume Microcapsules

The compositions of the present invention can comprise perfume oil encapsulated in a perfume microcapsule (PMC). The PMC can be a friable PMC. The term "PMC" and "perfume microcapsule" are used interchangeably and refers to a plurality of perfume microcapsules. Suitable perfume microcapsules and perfume nanocapsules can include: U.S. Patent Publication Nos. 2003215417 A1; 2003216488 A1; 2003158344 A1; 2003165692 A1; 2004071742 A1; 2004071746 A1; 2004072719 A1; 2004072720 A1; 2003203829 A1; 2003195133 A1; 2004087477 A1; and 20040106536 A1; U.S. Pat. Nos. 6,645,479; 6,200,949; 4,882,220; 4,917,920; 4,514,461; and 4,234,627; and U.S. Re. 32,713, and European Patent Publication EP 1393706 A1.

For purposes of the present invention, the term "perfume microcapsules" or "PMC" describes both perfume microcapsules and perfume nanocapsules. The PMCs can be friable (verses, for example, moisture activated PMCs). The PMCs can be moisture activated.

In one embodiment, the PMC comprises a melamine/formaldehyde shell. Encapsulated perfume and/or PMC may be obtained from Appleton, Quest International, or International Flavor & Fragrances, or other suitable source. In one embodiment, the PMC shell is coated with polymer to enhance the ability of the PMCs to adhere to fabric, as describe in U.S. Pat. Nos. 7,125,835; 7,196,049; and 7,119,057.

In one embodiment, the composition comprises a PMC but is free or essentially free or free of (neat) perfume. In such an embodiment, the composition may comprise less than about 20%, alternatively less than about 25%, alternatively from about 9% to about 20%, alternatively from about 9% to about 15%, alternatively from about 10% to about 14%, alternatively from about 11% to about 13%, alternatively combinations thereof, of PMC (including the encapsulated perfume) by weight of the composition. In such an embodiment, the perfume encapsulated by the PMC may comprise from about 0.6% to about 4% of perfume by weight of the composition.

In one embodiment, the composition consists essentially of: (a) from about 80% to about 91% by weight of the composition of polyethylene glycol, wherein the polyethylene glycol has a molecular weight from about 5,000 to about 11,000; and (b) from about 9% to about 20% by weight of the composition of a friable perfume microcapsule, wherein the perfume microcapsule comprises encapsulated perfume; wherein the composition is essentially free of free perfume; and wherein the composition is shaped in a pastille having a mass from about 0.95 mg to about 2 g. In such an embodiment, the perfume encapsulated by the PMC may comprise from about 0.6% to about 4% of perfume by weight of the composition.

In another embodiment, the composition comprises PMC and free perfume. In such an embodiment, the composition may comprise from about 1% to about 10%, alternatively from about 2% to about 12%, alternatively from about 2% to about 8%, alternatively from about 3% to about 8%, alternatively from about 4% to about 7%, alternatively from about 5% to about 7%, alternatively combinations thereof, of PMC (including the encapsulated perfume) by weight of the composition. In this embodiment, the perfume encapsulated by the PMC may comprise from about 0.6% to about 4% of perfume by weight of the composition.

In one embodiment, the composition may consist essentially of: (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of friable perfume microcapsule, wherein the perfume microcapsule comprises encapsulated perfume; wherein the composition is shaped in a pastille having a mass from about 0.95 mg to about 2 g. In this embodiment, the perfume encapsulated by the PMC may comprise from about 0.6% to about 4% of perfume by weight of the composition.

In one embodiment, the composition comprises (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of a friable perfume microcapsule, wherein the perfume microcapsule comprises encapsulated perfume; wherein the composition is shaped in a pastille, each of the pastilles has a mass from about 0.95 mg to about 2 g. Such a formulation is thought to provide for a balanced scent experience to the user of the composition. With the level of polyethylene glycol between about 80% and about 91% by weight of the composition, the about 2% to about 12% by weight of the composition of free perfume can provide for a pleasant scent experience to the user upon opening of the package containing the composition and as the user pours the composition into a dosing device and transfers the composition to her washing machine. That is the user can experience the scent at an appreciably detectable level but is not overwhelmed by the scent. Similarly, the about 2% to about 12% by weight of the composition of friable perfume microcapsule can provide physical and/or chemical stability of the pastille and for a sufficient quantity of friable perfume microcapsule to deposit on a user's clothing during washing when the pastilles are applied in the wash in a unit dose. Further, it can be beneficial for the composition to consist essentially of the above ingredients at the prescribed levels as additional components might interfere with the physical and/or chemical stability of the pastilles and recognizing that other components, such as surfactants, fabric softeners, or other such ingredients, might be delivered by other mechanisms, such as the detergent or dryer added product, and there would be the potential that the user might over apply such ingredients during washing and/or drying.

In yet another embodiment, the composition can comprise perfume microcapsule but is free or essentially free of other perfume carriers and/or free (neat) perfume. In yet still another embodiment, the composition may comprise a formaldehyde scavenger. In yet still another embodiment, the scent of the present composition is coordinated with scent(s) of other fabric care products (e.g., laundry detergent, fabric softener). This way, consumers who like APRIL FRESH scent, may use a pastille having an APRIL FRESH scent, thereby coordinating the scent experience of washing their laundry with their scent experience from using APRIL FRESH. The pastilles of the present invention may be sold as a product array (with laundry detergent and/or fabric softener) having coordinated scents.

Dye

The composition may comprise dye. The dye may include those that are typically used in laundry detergent or fabric softeners. The composition may comprises from about 0.001% to about 0.1%, alternatively from about 0.01% to about 0.02%, alternatively combinations thereof, of dye by weight of the composition. An example of a dye includes LIQUITINT BLUE BL from Millikin Chemical.

Free of Laundry Actives and Softeners

The composition may be free of laundry active and/or fabric softener actives. To reduce costs and avoid formulation capability issues, one aspect of the invention may include compositions that are free or essentially free of laundry actives and/or fabric softener actives. In one embodiment, the composition comprises less than about 3%, alternatively less than about 2% by weight of the composition, alternatively less than about 1% by weight of the composition, alternatively less than about 0.1% by weight of the composition, alternatively are about free, of laundry actives and/or fabric softener actives (or combinations thereof). A laundry active includes: detergent surfactants, detergent builders, bleaching agents, enzymes, mixtures thereof, and the like. It is appreciated that a non-detersive level of surfactant may be used to help solubilize perfume contained in the composition.

Pastilles

The composition of the present invention may be formed into pastilles by those methods known in the art, including methods disclosed in U.S. Pat. Nos. 5,013,498 and 5,770,235. The composition of the present invention may be prepared in either batch or continuous mode. In batch mode, molten PEG is loaded into a mixing vessel having temperature control. PMC is then added and mixed with PEG until homogeneous. Perfume is then added to the vessel and the components are further mixed for a period of time until the entire mixture is homogeneous. In continuous mode, molten PEG is mixed with perfume and PMC in an in-line mixer such as a static mixer or a high shear mixer and the resulting homogeneous mixture is then used for pastillation. PMC and perfume can be added to PEG in any order or simultaneously and dye can be added at a step prior to pastillation.

The pastilles may be formed into different shapes include tablets, pills, spheres, and the like. A pastille can have a shape selected from the group consisting of spherical, hemispherical, compressed hemispherical, lentil shaped, and oblong. Lentil shaped refers to the shape of a lentil bean. Compressed hemispherical refers to a shape corresponding to a hemisphere that is at least partially flattened such that the curvature of the curved surface is less, on average, than the curvature of a hemisphere having the same radius. A compressed hemispherical pastille can have a ratio of height to diameter of from about 0.01 to about 0.4, alternatively from about 0.1 to about 0.4, alternatively from about 0.2 to about 0.3. Oblong shaped refers to a shape having a maximum dimension and a maximum secondary dimension orthogonal to the maximum dimension, wherein the ratio of maximum dimension to the maximum secondary dimension is greater than about 1.2. An oblong shape can have a ratio of maximum dimension to maximum secondary dimension greater than about 1.5. An oblong shape can have a ratio of maximum dimension to maximum secondary dimension greater than about 2. Oblong shaped particles can have a maximum dimension from about 2 mm to about 6 mm, a maximum secondary dimension of from about 2 mm to about 4 mm.

In alternative embodiments of any of the formulations disclosed herein, each individual pastille can h-ave a mass from about 0.95 mg to about 2 g, alternatively from about 10 mg to about 1 g, alternatively from about 10 mg to about 500 mg, alternatively from about 10 mg to about 250 mg, alternatively from about 0.95 mg to about 125 mg, alternatively combinations thereof. In a plurality of pastilles, individual pastilles can have a shape selected from the group consisting of spherical, hemispherical, compressed hemispherical, lentil shaped, and oblong.

An individual pastille may have a volume from about 0.003 $cm^3$ to about 0.15 $cm^3$. A plurality of pastilles may collectively comprise a unit dose for dosing to a laundry washing machine or laundry was basin. A single unit dose of the pastilles may comprise from about 13 g to about 27 g, alternatively from about 14 g to about 20 g, alternatively from about 15 g to about 19 g, alternatively from about 16 g to about 18 g, alternatively combinations thereof. The individual pastilles forming the plurality of pastilles that make up the unit dose can each have a mass from about 0.95 mg to about 2 g. The plurality of pastilles can be made up of pastilles of different size, shape, and/or mass. The pastilles in a unit dose can have a maximum dimension less than about 1 centimeter.

The composition may be manufactured by a pastillation process. A schematic of a pastillation apparatus 100 is illustrated in FIG. 1. The steps of manufacturing according to such process can comprise providing the desired formulation as a viscous material 50. The viscous material 50 can comprise or consists of any of the possible formulations disclosed herein. In one embodiment, the viscous material 50 comprises: (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of friable perfume microcapsule, wherein the perfume microcapsule comprises encapsulated perfume. The viscous material 50 can be provided at a processing temperature less than about 20 degrees Celsius above the onset of solidification temperature as determined by differential scanning calorimetry.

In one embodiment, the PMC can be added as a slurry to the polyethylene glycol and free perfume to form the viscous material 50. The PMC can be added as a powder to the polyethylene glycol and free perfume to form the viscous material 50. The viscous material 50 is passed through small openings 10 and onto a moving conveyor surface 20 upon which the viscous material 50 is cooled below the glass transition temperature to form a plurality of pastilles 30. As illustrated in FIG. 1, the small openings 10 can be on a rotatable pastillation roll 5. Viscous material 50 can be distributed to the small openings 10 by a viscous material distributor 40. Pastilles can be formed on a ROTO-FORMER, available from Sandvik Materials Technology.

Package

A unit dose or a plurality of unit doses may be contained in a package. The package may be a bottle, bag, or other container. In one embodiment, the package is a bottle, preferably a PET bottle comprising a translucent portion to showcase the pastilles to a viewing consumer. In one embodiment, the package comprises a single unit dose (e.g., trial size sachet); or multiple unit doses (e.g., from about 15 unit doses to about 30 unit doses).

Dosing

The aforementioned package may comprise a dosing means for dispensing the pastilles from the package to a laundry washing machine (or laundry wash basin in hand washing applications). The user may use the dosing means to meter the recommended unit dose amount or simply use the dosing means to meter the pastilles according to the user's own scent preference. Examples of a dosing means may be a dispensing cap, dome, or the like, that is functionally attached to the package. The dosing means can be releasably detachable from the package and re-attachable to the package, such as for example, a cup mountable on the package. The dosing means may be tethered (e.g., by hinge or string) to the rest of the package (or alternatively untethered). The dosing means may have one or more demarcations (e.g., fill-line) to indicate a recommend unit dose amount. The packaging may include instructions instructing the user to open the removable opening of the package, and dispense (e.g., pour) the pastilles contained in the package into the dosing means. Thereafter, the user may be instructed to dose the pastilles contained in the dosing means to a laundry washing machine or laundry wash basin. The pastille of the present invention may be used to add freshness to laundry. The package including the dosing means may be made of plastic.

One embodiment can be a unit dose of a fabric treatment composition comprising a plurality of pastilles, wherein each pastille comprises: (a) from about 80% to about 91% by weight of the composition of polyethylene glycol, wherein the polyethylene glycol has a molecular weight from about 5,000 to about 11,000; (b) from about 2% to about 12% by weight of the composition free perfume; and (c) from about 2% to about 12% by weight of the composition of friable perfume microcapsule, wherein the perfume microcapsule comprises encapsulated perfume; wherein each pastille has a mass from about 0.95 mg to about 2 g; and wherein the plurality of pastilles has a mass from about 13 g to about 27 g to comprise the unit dose.

In one embodiment, the pastilles of the present invention can be administered to a laundry machine as used during the "wash cycle" of the washing machine (but a "rinse cycle" may also be used). In another embodiment, the pastilles of the present invention are administered in a laundry wash basin-during washing and/or rinsing laundry. In a laundry hand rinsing application, the pastille may further comprise an "antifoam agent" such as those available from Wacker. Antifoam agents (suds suppressing systems) are described in U.S. Patent Publication No. 20030060389 at 65-77.

Example

| Ingredient: | Grams in a 17 g unit Dose | % Weight of Composition |
|---|---|---|
| PEG 8000 | 15 | 88.24% |
| Free (neat) Perfume | 1 | 5.88% |
| Perfume Microcapsule[1] | 1 | 5.88% |
| (Encapsulated perfume)[2] | (0.32) | (1.88%) |
| Dye | 0.0025 | 0.015% |

[1]PMC is a friable PMC with a urea-formaldehyde shell from Appleton. About 50% water by weight of the PMC (including encapsulated perfume) is assumed.
[2]Encapsulated perfume (within PMC) assumes about 32% active.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package comprising:
a plurality of unit doses of a plurality of pastilles, the pastilles comprising a composition comprising polyethylene glycol repeat units and perfume, wherein:
individual pastilles of the plurality of pastilles comprise a flat surface and an opposing curved surface;
the individual pastilles of the plurality of pastilles comprise oblong-shaped pastilles;
the individual pastilles of the plurality of pastilles have a mass from about 0.95 mg to about 2 g;
the individual pastilles of the plurality of pastilles comprise pastilles of different mass; and
the package comprises a bottle.

2. The package of claim 1, wherein the individual pastilles of the plurality of pastilles have a mass of from about 10 mg to about 500 mg.

3. The package of claim 1, wherein the individual pastilles of the plurality of pastilles have a mass of from about 10 mg to about 250 mg.

4. The package of claim 3, wherein the individual pastilles of the plurality of pastilles comprise a maximum dimension and a maximum secondary dimension, and wherein a ratio of the maximum dimension to the maximum secondary dimension is greater than about 1.2 to about 2.

5. The package of claim 3, wherein the individual pastilles of the plurality of pastilles comprise a maximum dimension and a maximum secondary dimension, and wherein a ratio of the maximum dimension to the maximum secondary dimension is greater than about 1.5 to about 2.

6. The package of claim 1, wherein the individual pastilles of the plurality of pastilles have a mass of from about 125 mg to about 250 mg.

7. The package of claim 6, wherein the individual pastilles of the plurality of pastilles comprise a maximum dimension and a maximum secondary dimension, and wherein a ratio of the maximum dimension to the maximum secondary dimension is greater than about 1.2 to about 2.

8. The package of claim 6, wherein the individual pastilles of the plurality of pastilles comprise a maximum dimension and a maximum secondary dimension, and wherein a ratio of the maximum dimension to the maximum secondary dimension is greater than about 1.5 to about 2.

9. The package of claim 1, wherein the curved surface comprises a flattened portion.

10. The package of claim 1, wherein the package further comprises a dispensing cap.

11. A package comprising:
 a plurality of unit doses of a plurality of pastilles, the pastilles comprising a composition comprising polyethylene glycol repeat units and perfume, wherein:
  individual pastilles of the plurality of pastilles comprise a flat surface and an opposing curved surface;
  the individual pastilles of the plurality of pastilles comprise a first dimension and a second dimension orthogonal to the first dimension, wherein the ratio of the first dimension to the second dimension is greater than 1.2;
  the individual pastilles of the plurality of pastilles have a mass from about 0.95 mg to about 2 g;
  the individual pastilles of the plurality of pastilles comprise pastilles of different mass; and
  the package comprises a bottle.

12. The package of claim 11, wherein the individual pastilles of the plurality of pastilles have a mass of from about 10 mg to about 500 mg.

13. The package of claim 11, wherein the individual pastilles of the plurality of pastilles have a mass of from about 10 mg to about 250 mg.

14. The package of claim 13, wherein the individual pastilles of the plurality of pastilles comprise a maximum dimension and a maximum secondary dimension, and wherein a ratio of the maximum dimension to the maximum secondary dimension is greater than about 1.2 to about 2.

15. The package of claim 13, wherein the individual pastilles of the plurality of pastilles comprise a maximum dimension and a maximum secondary dimension, and wherein a ratio of the maximum dimension to the maximum secondary dimension is greater than about 1.5 to about 2.

16. The package of claim 11, wherein the individual pastilles of the plurality of pastilles have a mass of from about 125 mg to about 250 mg.

17. The package of claim 16, wherein the individual pastilles of the plurality of pastilles comprise a maximum dimension and a maximum secondary dimension, and wherein a ratio of the maximum dimension to the maximum secondary dimension is greater than about 1.2 to about 2.

18. The package of claim 16, wherein the individual pastilles of the plurality of pastilles comprise a maximum dimension and a maximum secondary dimension, and wherein a ratio of the maximum dimension to the maximum secondary dimension is greater than about 1.5 to about 2.

19. The package of claim 11, wherein the curved surface comprises a flattened portion.

20. The package of claim 11, wherein the package further comprises a dispensing cap.

21. A package comprising:
 a plurality of unit doses of a plurality of pastilles, the pastilles comprising a composition comprising polyethylene glycol repeat units and perfume, wherein:
  individual pastilles of the plurality of pastilles comprise a flat surface and an opposing curved surface;
  the individual pastilles of the plurality of pastilles comprise different shaped pastilles selected from the group comprising compressed hemispherical-shaped pastilles, tablet-shaped pastilles, oblong-shaped pastilles, pill-shaped pastilles and combinations thereof;
  the individual pastilles of the plurality of pastilles have a mass from about 0.95 mg to about 2 g;
  the individual pastilles of the plurality of pastilles comprise pastilles of different mass; and
  the package comprises a bottle.

22. The package of claim 21, wherein the individual pastilles of the plurality of pastilles have a mass of from about 10 mg to about 500 mg.

23. The package of claim 21, wherein the individual pastilles of the plurality of pastilles have a mass of from about 10 mg to about 250 mg.

24. The package of claim 23, wherein the individual pastilles of the plurality of pastilles comprise a maximum dimension and a maximum secondary dimension, and wherein a ratio of the maximum dimension to the maximum secondary dimension is greater than about 1.2 to about 2.

25. The package of claim 23, wherein the individual pastilles of the plurality of pastilles comprise a maximum dimension and a maximum secondary dimension, and wherein a ratio of the maximum dimension to the maximum secondary dimension is greater than about 1.5 to about 2.

26. The package of claim 21, wherein the individual pastilles of the plurality of pastilles have a mass of from about 125 mg to about 250 mg.

27. The package of claim 26, wherein the individual pastilles of the plurality of pastilles comprise a maximum dimension and a maximum secondary dimension, and wherein a ratio of the maximum dimension to the maximum secondary dimension is greater than about 1.2 to about 2.

28. The package of claim 26, wherein the individual pastilles of the plurality of pastilles comprise a maximum dimension and a maximum secondary dimension, and wherein a ratio of the maximum dimension to the maximum secondary dimension is greater than about 1.5 to about 2.

29. The package of claim 21, wherein the curved surface comprises a flattened portion.

30. The package of claim 21, wherein the package further comprises a dispensing cap.

* * * * *